United States Patent [19]

Theilacker et al.

[11] Patent Number: 5,138,138
[45] Date of Patent: Aug. 11, 1992

[54] HEATING SYSTEM FOR AN OPERATING TABLE

[75] Inventors: Wolfgang Theilacker; Hans-Peter Stihler; Axel Stihler, all of Stuttgart; Josef Burkert, Öhningen-Wangen, all of Fed. Rep. of Germany

[73] Assignee: Stihler Electronic Medizintechnische Gerate Prod. und Vertriebs-GmbH, Fed. Rep. of Germany

[21] Appl. No.: 548,927

[22] PCT Filed: Feb. 2, 1989

[86] PCT No.: PCT/DE89/00065
§ 371 Date: Jul. 26, 1990
§ 102(e) Date: Jul. 26, 1990

[87] PCT Pub. No.: WO89/06931
PCT Pub. Date: Aug. 10, 1989

[30] Foreign Application Priority Data

Feb. 3, 1988 [DE] Fed. Rep. of Germany ....... 3803139

[51] Int. Cl.⁵ .......................... H05B 3/06; H05B 1/02; H05C 3/00
[52] U.S. Cl. ..................... 219/528; 219/217; 219/218; 219/527; 219/546; 128/376
[58] Field of Search ............... 219/217, 218, 528, 529, 219/549, 211, 212, 527, 546; 128/600, 376; 5/421; 269/322

[56] References Cited

U.S. PATENT DOCUMENTS

| Re. 21,474 | 6/1940 | McCleary | 219/211 |
| 1,589,338 | 6/1926 | White | 219/211 |
| 1,648,631 | 11/1927 | Austin | 128/376 |
| 2,504,697 | 4/1950 | Kearsley | 219/217 |
| 2,745,942 | 5/1956 | Cohen | 219/211 |
| 3,114,825 | 12/1963 | Kilburn et al. | 219/211 |
| 4,540,878 | 9/1985 | Sato | 219/545 |
| 4,736,088 | 4/1988 | Bart | 219/211 |
| 4,788,417 | 11/1988 | Graflind | 219/528 |
| 4,825,868 | 5/1989 | Susa et al. | 219/553 |

FOREIGN PATENT DOCUMENTS

| 688786 | 10/1966 | Belgium . | |
| 715880 | 3/1938 | Fed. Rep. of Germany . | |
| 2056425 | 11/1970 | Fed. Rep. of Germany | 128/376 |
| 2308214 | 2/1973 | Fed. Rep. of Germany | 128/376 |
| 3119757 | 5/1981 | Fed. Rep. of Germany . | |
| 216627 | 2/1983 | Fed. Rep. of Germany . | |
| 2355426 | 6/1976 | France . | |

Primary Examiner—Geoffrey S. Evans
Assistant Examiner—Tuan Vinh To
Attorney, Agent, or Firm—Walter A. Hackler

[57] ABSTRACT

The heating system for an operating table comprises a multi-layer heating pad (2) having at least one heating segment (12a, 12b, 12c, 12d) which is adapted for being electrically heated and which is pervious to X-rays. A control and regulating unit (3) serving to control or regulate the heating current necessary for achieving an adjustable temperature of the heating pad (2) is connected to the heating pad (2). The heating pad (2) is equiped with a heating conductor (16) comprising a resistor (18) having a specific electric resistance and being wound in helical form about a carrier (17) made from an electrically non-conductive material which, regarding its mechanical properties, is rubber-elastic in the temperature range of between T=10° celsius to T=200° celsius. The different layers of the heating pad (2) are intimately bonded to form a composite material.

14 Claims, 6 Drawing Sheets

HEATING SYSTEM FOR AN OPERATING TABLE

The present invention relates to a heating system for an operating table having a multi-layer heating pad comprising at least one heating segment which is adapted for being electrically heated, which is pervious to X-rays and which can be connected to a control and regulating unit serving to control or regulate the heating current necessary for achieving an adjustable temperature.

Known heating pads for operating tables are relatively thick, either because their heating conductor consists of a rubber or plastic material which has been rendered conductive and which necessarily must have a certain sheet thickness to enable the sheet to absorb a current sufficient to achieve a reasonable heating capacity and/or because cushioning layers surrounding the heating pad proper are correspondingly thick. Thick or cushioned heating pads do not fold easily, their heat transmission deteriorates as their thickness rises, and they are also difficult to accommodate in the vessels available for sterilization. Besides, known heating pads are largely unsuited for sterilization because they are built up from separate unconnected layers and because the components used would be damaged by the sterilization process.

A heating pad for operating tables of the described type has been known from a certain leaflet entitled VITALMED Thermoauflage VIT 2000 as from BE-A-688 786.

The known heating pad provides, however, the disadvantage that the sheet-like heating conductors are suited for a limited heating capacity only and would become intolerably thick and rigid if the heating capacity were further increased. The existing form of a heating pad is already so thick that it cannot be folded together or rolled up. In addition, it comprises certain components which may damage the layered structure of the heating pad if the latter were rolled up. The components of the pad are not sufficiently temperature-resistant to enable the heating pad to be sterilized.

Moreover, for controlling the temperature of the heating pad known as Tetalmed Thermoauflage VIT 2000, the temperatures recorded within the same heating segment are compared in the heating pad proper, and the control and regulating unit is then supplied with a single actual temperature value for each heating segment.

Another heating pad has become known under the trade name of "Thermomaquet 1004.64".

This heating pad is not subdivided into separately operated heating segments and comprises in addition an aluminium film covering as a single sheet almost the full surface of the heating pad, thus counteracting any expansion of the individual layers of the heating pad. Consequently, this heating pad does not easily fold or roll up, and in addition it is unsuited for sterilization.

Further, a control system for controlling the surface temperature of a heated cushion, in particular a cushion for an operating table, has been described by DE-OS 31 19 757. The sensor used in this cushion can be moved relative to the latter, exhibits a flat design and is enclosed inside the cushion by rigid copper plates.

It is, therefore, a disadvantage of this known heating pad that monitoring of the heating capacity, which would be required under safety aspects, is possible only to a limited degree. Another disadvantage of this pad resides in the fact that the temperature sensors, being enclosed by copper plates, are impervious to X-rays and produce undesirable contrasts on X-ray images. It is therefore necessary to arrange temperature sensors of this type in the marginal areas of the heating pad which means, however, that they cannot record the actual temperature values prevailing in the heating zone. In addition, the plate-like structure of the temperature sensors and the multi-layer structure of the heating pad proper are not suited to enable the heating pad to be rolled up tightly for sterilization purposes.

DE-PS 715 880 describes a heating conductor for a flexible electric heating unit comprising a heating conductor whose carrier thread may consist of asbestos or any other insulating material. The carrier thread is surrounded by one or more bare or insulated heating wires which are wound about the thread in helical windings. The known heating conductor is connected with the disadvantage that its carrier thread does not stretch so that the carrier thread, with the resistor wire wound about it, may be damaged by the least stress. As experience shows heating pads for operating tables should be very flexible and thin so as to adapt themselves easily to different positions of the operating table, without adding undesirable thickness, this known heating conductor is unsuited for use in heating pads for operating purposes.

Finally, a heating pad for medical applications has been known from DD-PS 216 627. This pad is said to be flexible and to be suited for sterilization, and also to meet the requirements of technical safety in medical applications. From FIG. 2 of this printed publication it can be derived that this heating pad is built up from a plurality of individual layers, which are loosely connected and held together by an envelope made from a thin imitation leather film. The heating conductor consists of a metal gauze. The desired layered structure is neither steam-tight, nor are the different components of the heating pad designed or protected in such a manner that the heating pad as a whole is suited for being rolled up or sterilized. Commercial metal gauzes do not stand bending and are not pervious to X-rays, either. In addition, no high specific heating capacity can be achieved with the described metal gauze.

SUMMARY OF THE INVENTION

Now, it is the object of the present invention to improve a heating pad of the type described above in such a way that while providing an increased heating capacity it can be kept as thin as possible, and that the structure of the heating pad provides the best possible protection for the installed components, and permits safe monitoring of the heating power.

This object is achieved according to the invention by the fact that the heating pad is equipped with a heating conductor comprising a resistor having a specific electric resistance and being wound in helical form about a carrier made from an electrically non-conductive material which, regarding its mechanical properties, is rubber-elastic in the temperature range of between $T=10°$ celsius to $T=200°$ centigrade.

Consequently, the heating pad according to the invention provides the substantial advantage that it can be made extremely thin without having to restrict the heating capacity of the heating pad. For example, the heating conductor may have a diameter as small as 1.3 mm. By winding the heating conductor about the carrier in spiral form and giving the carrier rubber-elastic properties, one enables the conductor to stretch in the axial direction. The capability of the carrier to stretch is limited only by the expansion properties of the carrier material. In addition, the carrier gets thinner when stretching in the axial direction so that any forces developed in this case will not be transmitted to the conductor.

The heating conductor is highly flexible, so that it will adapt to any deformations of the heating pad, and in addition no special protective arrangements must be provided for the heating conductor in the layered structure of the heating pad according to the invention. The pad can do without any additional layers or envelopes intended to protect the heating conductor, a fact which favors the thin design of the heating pad according to the invention. In addition, the high flexibility of the heating conductor allows the conductor to be run through the heating pad in a way permitting optimum monitoring of the heating capacity, by means of suitable components.

If the heating pad has a total thickness of approx. 5 mm in the area of the heating segments and of approx. 8 mm in the marginal area, then the pad remains flexible and capable of being rolled up tightly. The manufacture of a heating pad as thin as that, with satisfactory heating capacity, is rendered possible only by the combination of the described features.

The object according to the invention is further achieved by the fact that the heating pad is formed from different layers which are intimately bonded to form a composite material.

By cross-linking the adjacent layer surfaces on intimate contact is established between the layers which will remain unaffected even when the heating pad gets deformed. This is a precondition for efficient heat transmission from the heating conductor to the adjacent layers. The fact that cross-linking of the materials occurs also between the carrier of the heating conductor and the layer surrounding it makes it possible to run the heating conductor in the heating pad in very narrow loops, for example according to a meander pattern. The heating conductor is fixed in place in the heating pad so that any mutual contact between the individual heating conductors can be excluded. This constructional design of the heating pad according to the invention guarantees on the one hand increased heating capacity on limited space and on the other hand efficient protection of the heating conductor, and provides in addition the possibility to safely monitor the heating capacity of individual heating conductor sections.

The composite structure of the material of the heating pad makes the latter absolutely vapor-tight, which means that it can be sterilized safely with saturated steam under pressure, in line with the medical rules for the sterilization of instruments, etc., without any risk of damage to the components arranged inside the heating pad.

According to a further development of the invention, the heating pad comprises a heating conductor which is run along the center plane of the heating pad which is regarded as neutral under bending aspects.

This provides the advantage that the heating conductor cannot be damaged by longitudinal and/or transverse forces acting on the heating pad. Even if a small bending radius is selected for rolling up the heating pad, this cannot damage the heating conductor.

According to a preferred embodiment of the invention, the heating conductor is composed of a carrier, made preferably from a silicon rubber, and an aluminium wire of circular cross-section serving as conductor.

The carrier consisting of silicon rubber, it is highly rubber-elastic in the operating temperature range of the heating pad and has the effect, in combination with the circular cross-section of the conductor and the helical shape of the conductor on the carrier, that the aluminium conductor, which normally does not stand high mechanical stresses, assumes elastic properties. This structure of the heating conductor according to the invention finally provides the preconditions required for permitting the production of heating pads for operating tables which are thin, offer a high heating capacity, are pervious to X-rays and equipped with a heating system that can be safely monitored.

Further, the heating conductor is embedded in a first layer having a thickness equal to the outer diameter of the heating conductor or, preferably, being 10% to 20% thicker than the outer diameter of the heating conductor.

This provides the advantage that perfect, stable and full-surface cross-linking between the first layer and an adjacent layer is achieved during vulcanization.

According to a further development of the invention, the first layer is an electrically non-conductive silicon rubber layer having good thermal conductivity and offering, in the composite material, a rubber-elastic behavior similar to that of the carrier. To make the first layer from a silicon rubber provides the advantage that the layer has a thickness similar to that of the carrier material so that the composite structure between the carrier of the heating conductor and the first layer can be achieved in a simple manner. The identical rubber-elastic properties exclude any material distortions in the heating pad during expansion of the latter.

According to a further development of the invention, the first layer is surrounded by a second layer of silicon caoutchouc, the first and the second layers have largely identical material properties, and the elastic expansion of the first and the second layers is limited by a fabric layer arranged between the first and the second layers and forming a composite structure with the adjacent layers.

This arrangement provides the advantage that a composite structure between the first and the second layers can be achieved in a simple manner by vulcanization even if, for example, different silicon caoutchouc materials are selected for the first and the second layers. This is so because the properties of the materials remain almost identical, as regards their fabrication. For example, the silicon rubber material of the second layer may be selected to be softer and more resistant at the surface than the silicon rubber material of the first layer. One thereby achieves improved comfort for the patient and higher resistance of the heating pad to cleaning and mechanical influences.

The fabric layer makes it possible to limit the rubber-elastic properties of the silicon rubber layers in a convenient manner. In addition, it improves the inherent stability of the heating pad. If a glass fiber mat, for example, is selected as fabric layer, then a composite structure is obtained during vulcanization of the heating pad also between the silicon rubber layers and the fabric layer.

According to a further improvement of the invention, the second layer is an electrically non-conductive silicon rubber layer which is reinforced in its marginal areas and whose surface forms a composite structure with an additional, third layer capable of eliminating electric charges. The reinforcement of the second layer in its marginal area has the effect to further increase the inherent stability of the heating pad, without restricting the deformability of the heating pad. The heating pad is thus given sort of a frame. The electrically non-conductive second layer further forms a composite structure with a third layer having electrically non-conductive properties. The third layer is capable of eliminating electric charges.

The heating pad further comprises temperature sensors, preferably two semiconductor resistors with high negative temperature coefficients per heating segment, which are arranged in the heating pad between the meander-like lines of a heating conductor.

This arrangement provides the advantage that on the one hand the heating conductor is guided safely and retained against displacement in the thin first layer and good heat transmission is ensured between the first layer and the heating conductor, while on the other hand the temperature sensors (NTC), being vulcanized into the first layer, are also held safely, exactly and free from displacement, in one plane with the heating conductor. Moreover, the NTC temperature sensors do not restrict the flexibility of the first layer, the sensors being of a type not much bigger than a needle head.

According to a further improvement of the invention, the connection wires of the temperature sensors are pervious to X-rays and exhibit rubber-elastic properties.

This feature provides the advantage that the temperature sensors can be arranged safely at any point in the first layer of the heating pad. Although the NTC temperature sensors proper do not consist of materials pervious to X-rays, they do not make themselves felt as disturbing in an X-ray picture being only very small. In contrast, the shadows produced by the feed and output lines of the NTC temperature sensors would make themselves felt as disturbing in the evaluation of X-rays as such shadows may extend over the full length or width of the X-ray. When an electric conductor such as the heating conductor according to the invention is chosen for the feed and output lines of the NTC temperature sensors, then the NTC temperature sensors can be wired safely in the heating pad without being visible in an X-ray picture. The lines are flexible and rubber-elastic and are, therefore, not susceptible to damage by deformations of the heating pad.

According to another further development of the invention, the electric wires of the heating conductors of the heating segments are connected in parallel and the electric conductors of the temperature sensors are united in pairs, and electrostatic charges are eliminated by an electric conductor which is connected to a third layer.

The described wiring of the heating segments enables any trouble to be identified very quickly, and in addition only a single electric feed and output line has to be run through the heating pad. The particular wiring of the NTC temperature sensors permits safe temperature measurements in the heating pad even when the heating pad is covered up by one third only.

The arrangement of the third layer, which is capable of eliminating electrostatic charges, excludes any building-up of electrostatic charges or charges caused by high-frequency currents in the area of the heating pad as such charges can be eliminated safely by this third layer. Further, there is the possibility to provide a shielding which can be connected to this third layer in an electrically conductive manner.

According to a further developement of the invention, the bunched electric conductors are provided, at their point of exit from the first layer, with a vulcanized anti-kink device, preferably provided with a folding notch.

This feature offers the advantage that when the heating pad is rolled up or folded together, the bunched conductors can be applied closely to the heating pad without any risk for the conductors to break.

According to a preferred further development of the invention, the bunched conductors are surrounded outside the first layer by a flexible sheathing which is temperature-resistant in the temperature range of $T = 10°$ Celsius to $T = 200°$ Centigrade, and the bunched conductors terminate in a plug which can optionally be sealed by a cap.

This arrangement provides the advantage that the heating pad, together with the cable fixed thereon by vulcanization and the attached plug can be rolled up tightly and can be sterilized. The cap provides a pressure-tight seal for the open side of the plug so that any humidity is prevented from entering the plug.

Preferably, the marginal areas of the lower surface of the heating pad are provided with closure tapes, preferably in the form of self-locking tapes and/or snap-fastener tapes.

This feature provides the advantage that in case of need additional segments can be attached to the heating pad in a simple and safe manner.

According to a further development of the invention, the heating pad is designed in the form of a heating pad with slot, the latter extending from one narrow side over part of the longitudinal extension of the heating pad and providing the possibility to attach and/or connect diverse additional segments.

This arrangement provides the advantage that when the segments are to be placed on or around the patient's limbs, they cannot get dislodged and will cover the whole patient without leaving any gaps. This helps improve the patient's comfort and avoid excessive heat losses through the patient's skin.

Further, the control and regulating unit comprises a plurality of inputs for lines from the heating pad and the segments.

This arrangement provides the advantage that different forms of heating pads can be composed from separate components as required. Given the fact that these components have their own segments and supply lines, they can also be operated, and sterilized, separately from the basic heating pad.

According to a further development of the invention, the heating pad and/or the segments can be covered by an insulating mat.

This feature provides the advantage that the heating pad according to the invention can be used also when high-frequency surgery instruments are used for operating purposes. The electric instruments then do not interfere with each other, and the safe function of the high-frequency surgery instruments, and of the heating pad, too, is guaranteed.

According to a further development of the invention, the regulating and control unit is equipped with a display comprising a first and a second pre-selector switch for the temperature of the heating pad and of the segments, and with luminous fields indicating the operative state, the operating condition and any faulty condition of the individual segments.

This feature provides the advantage to make monitoring of the heating pad simple and its operation easy and clear.

Thus, the heating system for operating tables meets all the sophisticated requirements that have to be fulfilled by operating equipment. The heating pad is easy to handle, it does not add excessive thickness to the operating table, being exceptionally thin, it can be deformed in longitudinal and transverse direction without any damage to the heating pad itself and without any deterioration of its heating capacity. The size of the heating pad can be increased at desire, the individual heating pads and/or segments may be heated and temperature-controlled by separate regulating and control units, and the individual heating pads and/or segments are particularly flexible and can be rolled up very tightly, and they are suited for sterilization in commercial sterilization vessels. The heating pad is flame-resistant.

Other advantages of the invention will appear from the following specification and the attached drawing. The features that have been described above and will be explained hereafter may be used according to the invention either individually or in any combination thereof. The described embodiments of the invention are not to be understood as a comprehensive list of possible embodiments, but are mentioned only by way of example.

BRIEF DESCRIPTION OF THE DRAWINGS

The invention will now be described in more detail by way of certain embodiments illustrated in the drawing in which.

Figure 1:
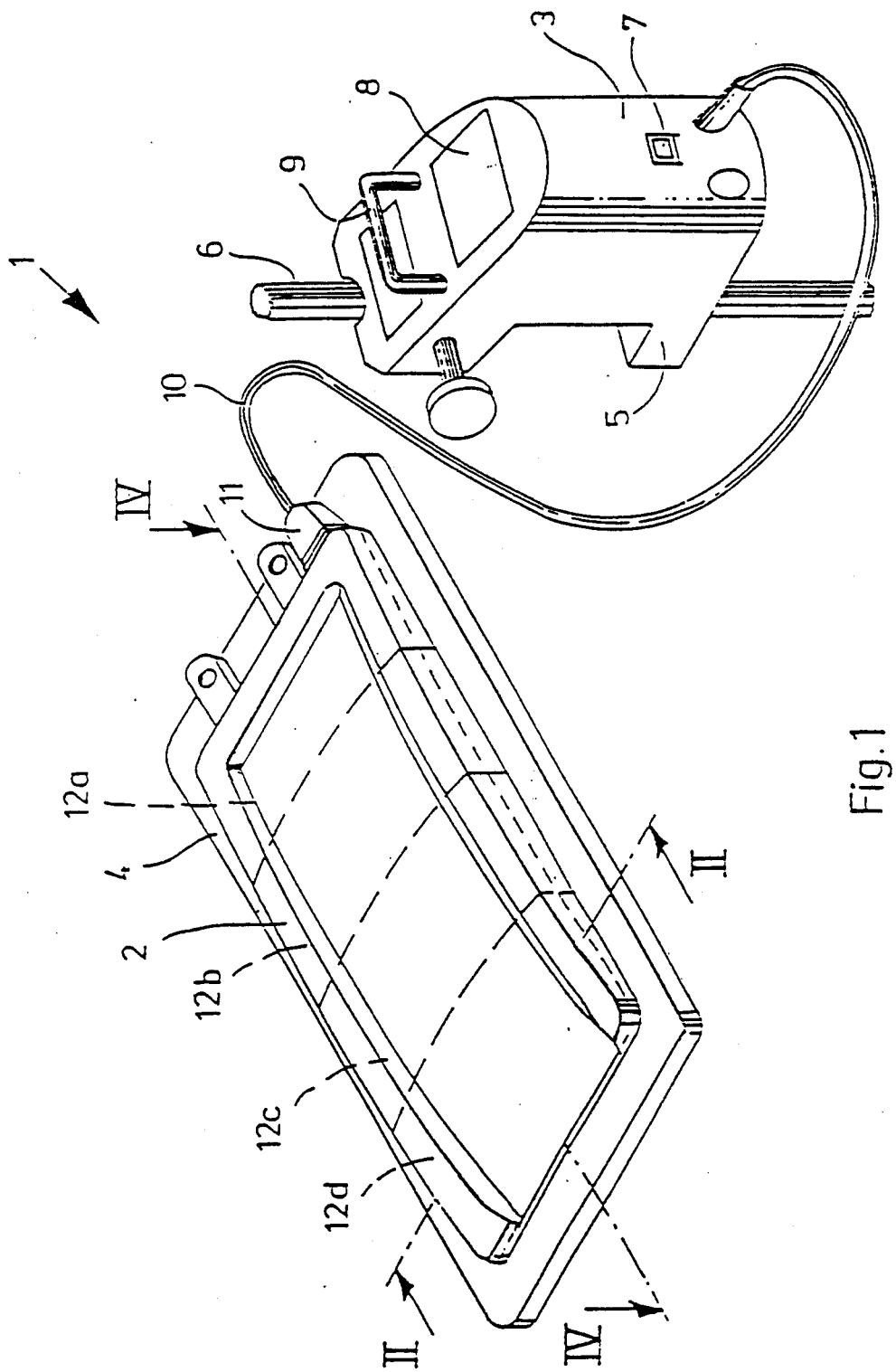
FIG. 1 shows a complete set-up of the different components of the heating system for an operating table according to the invention.

The different figures of the drawing show the object of the invention partly in a very diagrammatic form and not to scale. Some of the elements shown in the figures are greatly enlarged so that their structure can be seen more clearly.

DETAILED DESCRIPTION

FIG. 1 shows a heat system 1 for operating tables (not shown) composed of a heating pad 2, a control and regulating unit 3 and an insulating mat 4. If required, the heat system 1 can be supplemented by an additional insulating mat 4 placed on top of the heating pad 2 and/or below the heating pad 2. For the sake of clarity, only one insulating mat 4 is illustrated in FIG. 1. The marginal areas of the heating pad 2 according to the invention are reinforced in the manner of a frame. The control and regulating unit 3 comprises a mounting claw 5 serving to fix the unit on a rod 6, for example an infusion stand. The design of the housing of the control and regulating unit 3 is, however, such that the unit can be placed directly on a supporting surface. The heating system 1 can be switched on by means of a master switch 7 arranged at the front of the control and regulating unit 3. The front surface of the control and regulating unit 3 tapers a little towards the rear and carries a display 8. A carrying handle 9 integrated into the lid of the housing enables the control and regulating unit 3 to be carried safely and to be held safely during mounting.

The heating pad 2 is electrically connected to the electric control unit 3 by a cable 10. A socket arranged at the rear of the control and regulating unit 3 serves for connecting the heating pad 2 and the control and regulating unit 3 to the mains.

The end of the cable 10 adjacent the heating pad 2 is fixed to the heating pad 2 by vulcanization. The firm connection between the heating pad 2 and the cable 10 is equipped with an anti-kink device which may be provided, for example, with a folding notch 10.

The heating pad 2 proper is subdivided into four heating segments 12a, 12b, 12c, 12d which are heated and temperature-controlled through the control and regulating unit 3.

Figure 2:
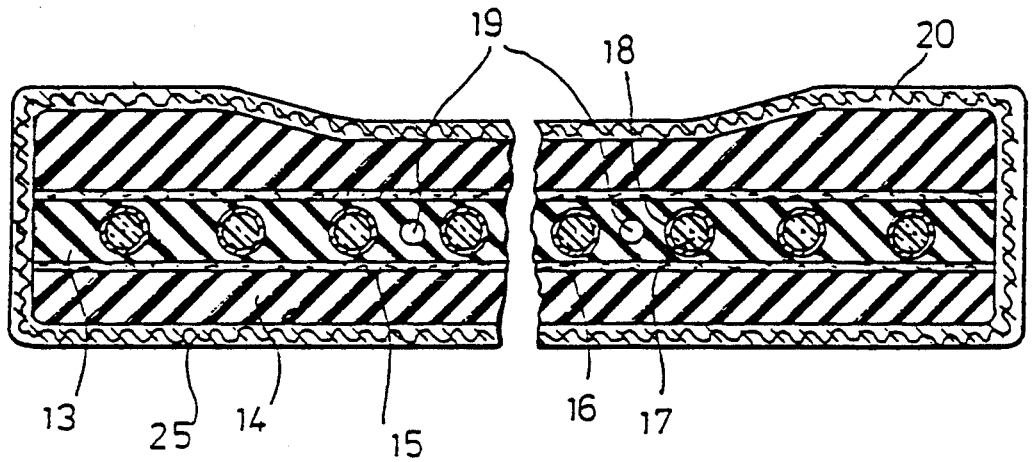
FIG. 2 shows a cross-sectional view, taken along line II—II in FIG. 1, of a heating pad of a heating system according to the invention.

FIG. 2 illustrates the layered structure of the heating pad 2, showing a cross-section along line II—II in FIG. 1. The heating pad 2 is composed of an electrically non-conductive first layer 13, a second layer 14, a fabric layer 15 and a third layer 25. The first layer 13, the second layer 14, the fabric layer 15 and the third layer 25 form together a composite which has been achieved by vulcanization of the layers. The first and the second layers 13, 14 are electrically non-conductive. The third layer 25 is capable of eliminating electrostatic charges. The fabric layer 15 must consist of a material which is capable of forming a composite with the other layers during the vulcanization.

The fabric layer 15, which preferably consists of a glass fiber mat, acts to limit the rubber-elastic properties of the first and second layers 13, 14 which consists of a silicon rubber.

The first layer 13 consists of a silicon rubber mixture which in the vulcanized condition has good heat transmission properties and is capable of forming a close and safe sheathing around the components. The second layer 14 consists of a silicon rubber mixture which is abrasion-resistant and which determines the degree of softness of the heating pad 2. The third layer 25, also a silicon rubber mixture, becomes conductive to a certain degree only after the addition of certain admixtures 20. Such conductive admixtures 20 may consist, for example, of soot or graphite particles. By enriching the third layer 25 with conductive admixtures 20 one attains an electric resistance for the layer 25 in the area of between 50,000 Ohm and 1M Ohm.

The electrically non-conductive first layer 13 includes heating conductors 16 which are embedded therein by vulcanization and which consist of a carrier 17 and an electric conductor 18. Temperature sensors 19 (NTC), which are embedded between the heating conductors 16 in the first layer 13 by vulcanization, serve to pick-up the temperature of the heating conductors 16 and to transmit it as actual value to the regulating and control unit 3.

FIG. 2 shows the different layers in a representation not true to scale. The thickness of the third layer 25, which surrounds the heating pad 2 not only on its longitudinal sides, but also on its transverse sides and which does not in any way influence the mechanical and chemical properties of the heating pad 2, amounts to a few μ meters only. The layers 13, 14, as well as the fabric layer 15, have a thickness in the mm range. The total thickness of the heating pad 2 is equal to approx. 5 mm in the area of the heating segments and to approx. 8 mm in the marginal area.

Figure 3:
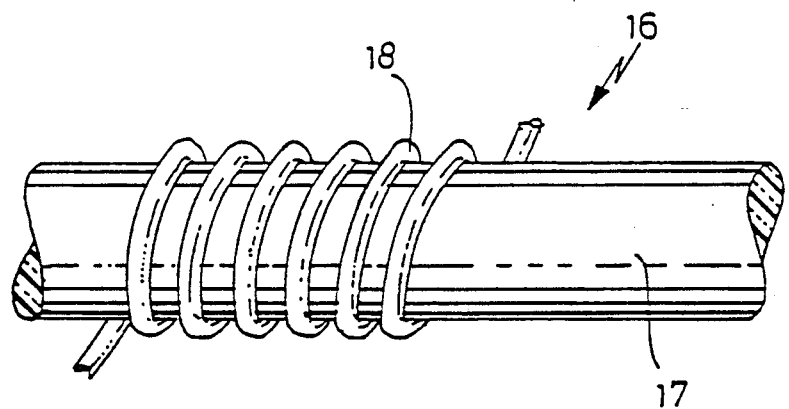
FIGS. 3 and 3A shows part of a heating conductor of the heating pad.

FIG. 3 shows a greatly enlarged portion of the heating conductor 16, in the form in which it is vulcanized into the first layer 13. The carrier 17 consists of a rubber-elastic, electrically non-conductive material which has a circular cross-section and a diameter of approx. 1.2 mm as used in this application. However, it is of course also possible to use other carriers having a diameter of 1 mm to 1.5 mm. The described embodiment of the invention makes use, for the carrier 17, of a silicon rubber material which exhibits rubber-elastic properties in a wide temperature range.

The electric conductor 18, being wound closely around the carrier 17, consists of an aluminium wire or an aluminium strip having a thickness of approx. 0.2 mm to 0.5 mm, depending on the particular design of the heating conductor 16. The carrier 17 gives the thin aluminium wire of circular cross-section the required rigidity, while the combination of the helically wound conductor 18 and the rubber-elastic carrier 17 enables the conductor 18 to be extended in axial direction and to be loaded in transverse direction, without any risk of damage to the heating conductor 16.

Figure 3A:
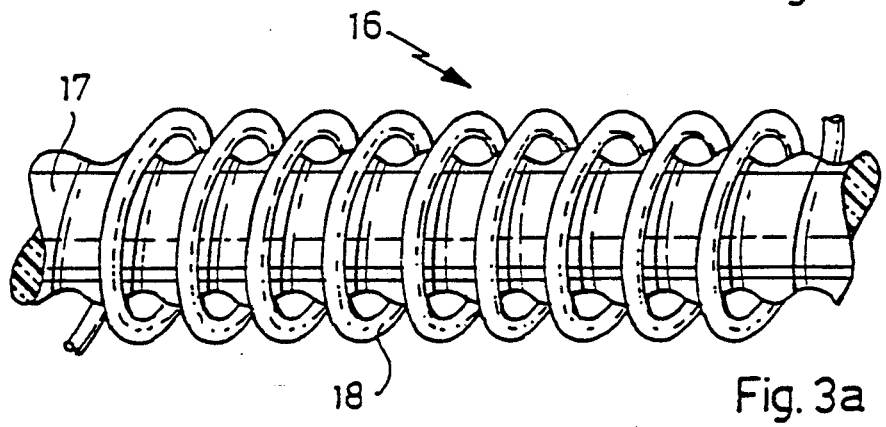

FIG. 3a is a greatly enlarged representation illustrating the manner in which the conductor 18 is wound about the carrier 17. It is only for the purpose of clarity of the representation that the conductor 18 is not in intimate contact with the carrier 17 in this figure. In reality, the different conductor sections of the conductor 18 are in form-locking engagement with the carrier 17.

Figure 4:
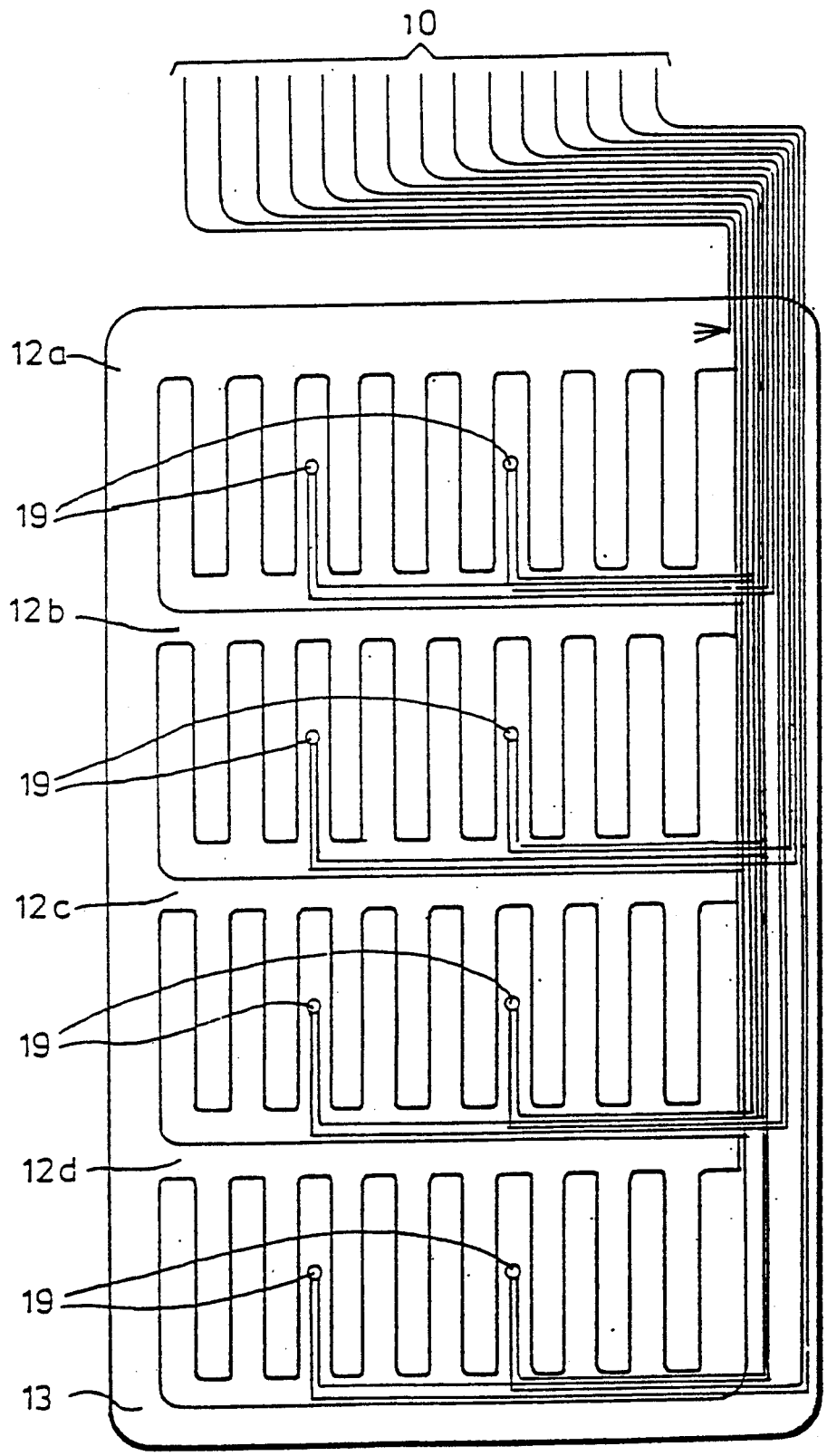
FIG. 4 shows a sectional top view of the heating pad, along line IV—IV in FIG. 1.

FIG. 4 shows a sectional representation of the heating pad 2, taken along line IV—IV in FIG. 1. The top view illustrates the arrangement of the different heating segments 12a, 12b, 12c, 12d in the first layer 13, the location of the temperature sensors 19, the arrangement of the heating conductors in the individual heating segments 12a, 12b, 12c, 12d and the manner in which the conductors and/or the wiring of the heating conductors 16 and the lines of the temperature sensors 19 are run. The electric conductors emerge, by way of example, at the right top end of the first layer 13 where they are united to form the cable 10. At their point of exit from the first layer 13, the electric conductors are once more fixed to the heating pad 2 by vulcanization so that no pulling forces will be transmitted to the electric conductors of the heating conductor 16 and/or to the electric conductors of the temperature sensors 19 in the first layer 13, for example if the cable 10 should be kinked or subjected to pulling forces.

In the embodiment represented by way of example in FIG. 4, the heating segments 12a, 12b, 12c, 12d are connected in parallel, electrically. The electric conductors of the temperature sensors 19 are united in pairs and leave the first layer 13 in this condition. A further conductor is provided for shielding the cable 10 and the heating pad 2 and is electrically connected to the third layer 25.

The particular manner in which the heating segments 12a, 12b, 12c, 12d and the temperature sensor 19 are wired, guarantee a high degree of safety and reduce the 15-wire bunched conductor, the cable 10, to a limited number of individual wire conductors.

The temperature sensors 19 are positioned in the individual heating segments 12a, 12b, 12c, 12d in the same plane as the heating conductors 16 and are connected to electric conductors which, in the illustrated embodiment, correspond to the heating conductor 16, and which are pervious to X-rays.

The meander pattern of the heating conductors 16 illustrated in FIG. 4 is to be understood as an example only it being understood that the conductor may be run through the first layer 13 along a different pattern, if needed.

The folding notch 11 at the point of exit of the cable 10 from the heating pad 2 gives the cable 10 great freedom to move relative to the heating pad 2, free from pulling and compression stresses.

Figure 5:
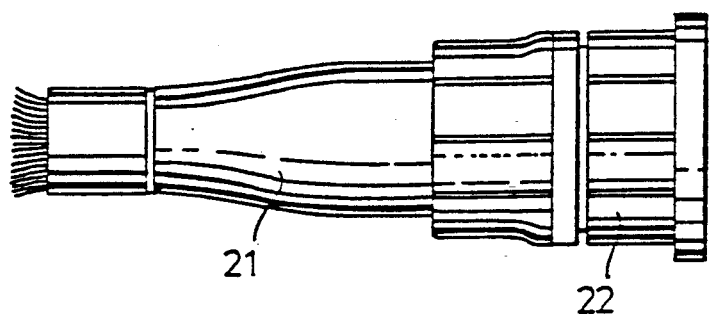
FIG. 5 shows a plug with cap of the type employed at the end of the line remote from the heating pad, during sterilization of a heating pad.

FIG. 5 shows a plug 21 of the type provided at that end of the cable 10 which is remote from the heating pad 2. The free end of the plug 21 can be sealed by a cap 22 which can be fitted thereon in pressure, gas and liquid-tight fashion. The cap 22 is fitted on the plug 21 when the heating pad is to be sterilized together with its cable 10 and the plug 21. With the cap 22 removed, the plug 21 can be plugged into a matching socket arranged at the rear of the control and regulating unit 3.

Figure 6:
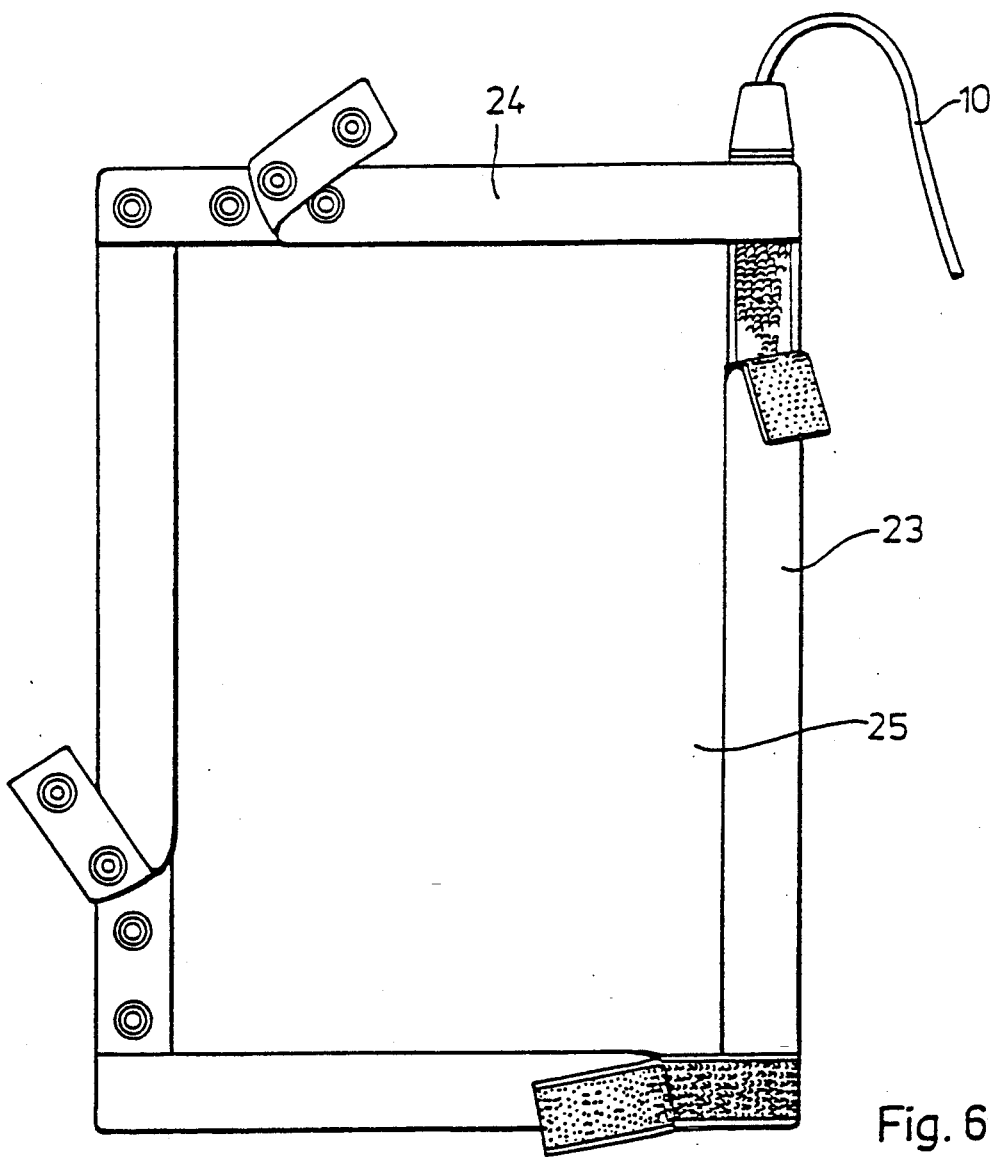
FIG. 6 shows the bottom surface of a heating pad.

FIG. 6 shows a plan view of the lower surface of the heating pad 2, i.e. the surface of the conductive third layer 25. In the example illustrated in this figure, the marginal areas of the conductive third layer 25 are equipped with closure tapes which are fixed thereto either by bonding or by vulcanization. The closure tapes consist, preferably, of self-locking tapes 23 or snap-fastener tapes 24 by means of which additional heating pads can be attached to the heating pad 2. This enables the size of the heating pad 2 to be increased in a simple manner.

Figure 7:
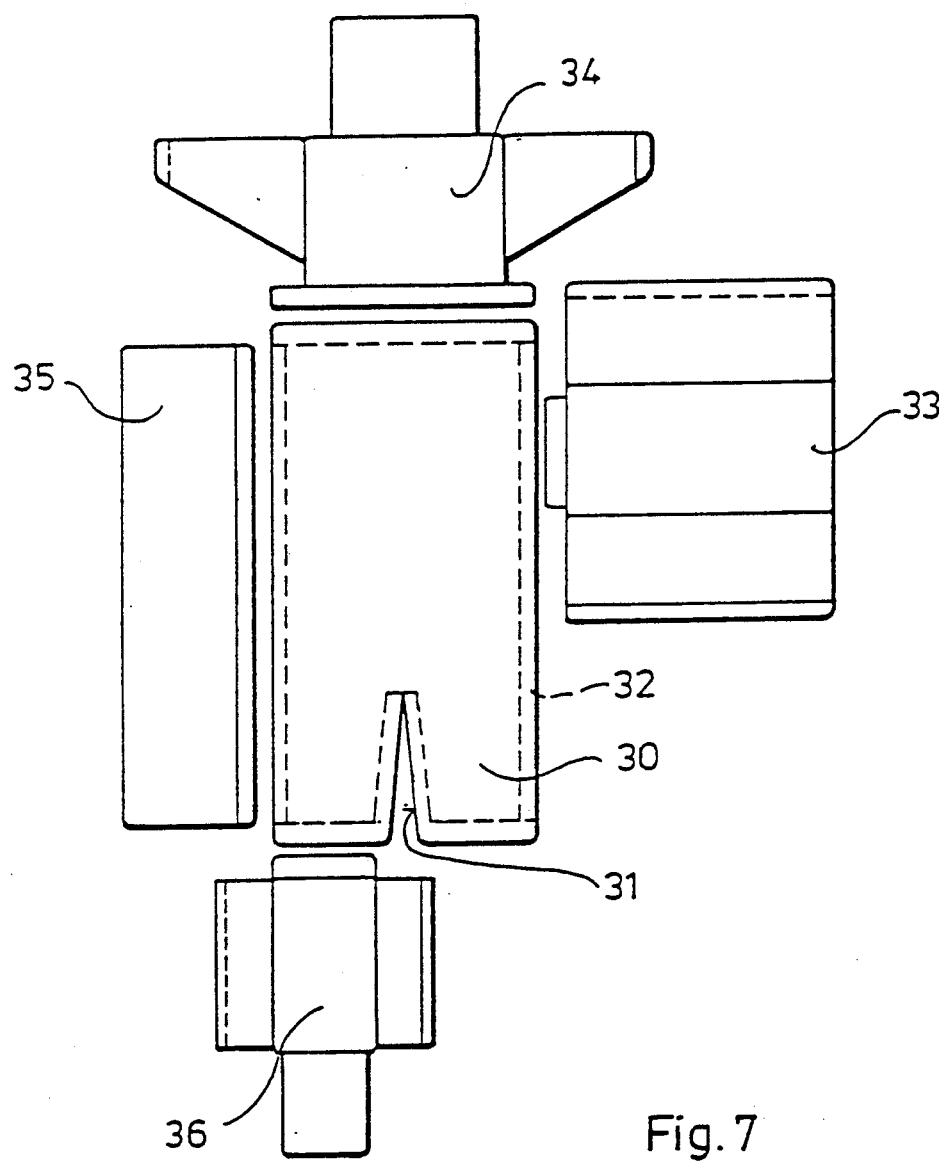
FIG. 7 shows a top view of other embodiments of a heating pad and of individual segments.

FIG. 7 shows a very diagrammatic representation of another embodiment of a heating pad 30, and other embodiments of segments 33 to 36.

The heating pad 30 is provided, in the marginal area of its bottom surface, with closure tapes 32 by means of which the segments 33, 34, 35 and 36 can be buttoned down on or attached to the heating pad 30. The heating pad 30 is provided with a slot 31 extending from the center of one of its narrow ends. The illustrated example of the segment 33 is designed in such a way that on the one hand it can be attached to the heating pad 30 while on the other hand it can be wrapped around the patient's arms. The segment 34 is shaped in such a way that it will easily wrap around the patient's head, without getting dislodged. The segment 35 has a rectangular shape and may be used as a cover for a patient. In the area of the patient's legs and feet, the segment 36 will be given a shape suitable of being wrapped tightly about the patient's foot and leg.

The possible designs of the segments 33 to 36 are by no means limited to the illustrated embodiments which are described only by way of example.

Figure 8:
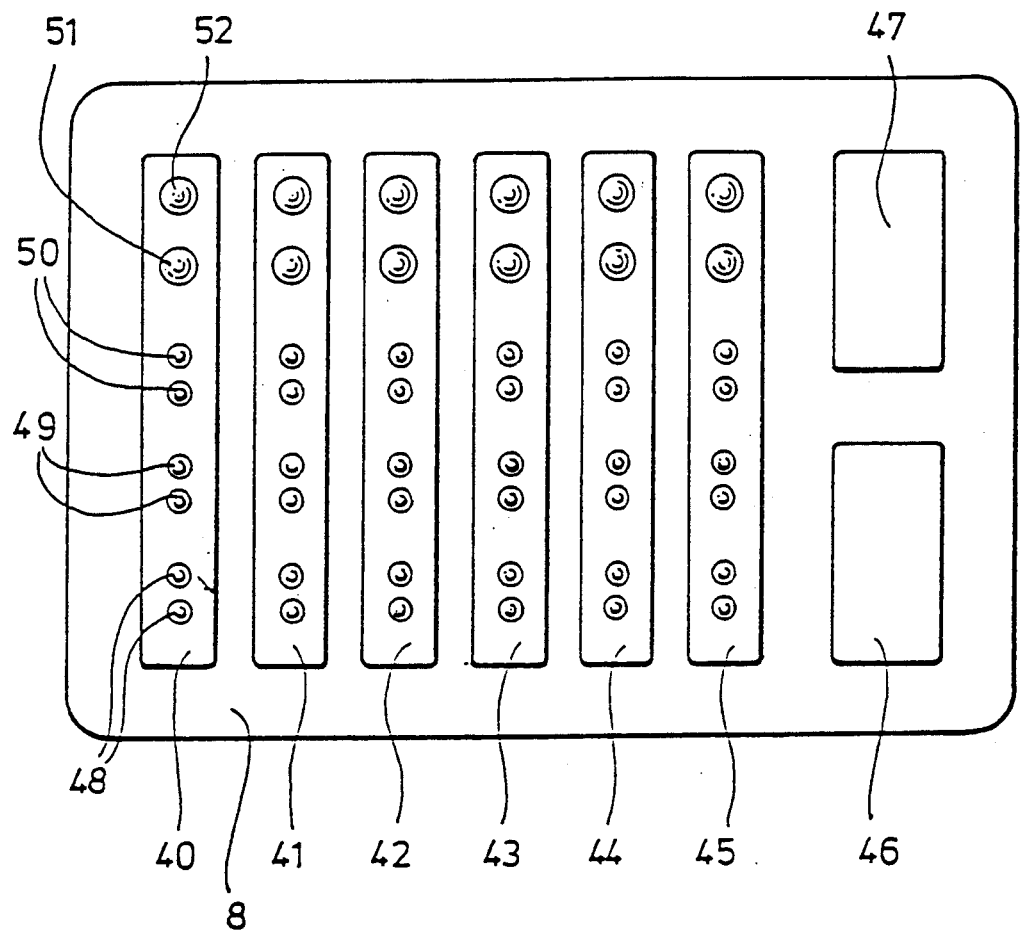
FIG. 8 shows one embodiment of the display of a control and regulating unit of a heating system for operating tables according to the invention.

FIG. 8 shows an example of a display 8 of the regulating and control unit 3. The display 8 comprises luminous fields 40 to 45 each assigned to one heating segment 12a, 12b, 12c, 12d. For example, the luminous field 40 may be assigned to the heating segment 12a, the luminous field 41 to the heating segment 12b, the luminous field 42 to the heating segment 12c and the luminous field 43 to the heating segment 12d. The luminous fields 44 and 45 are freely assignable and may also be assigned to additional heating pads 2/30 or segments 33 to 36. The display 8 comprises further a first switch 46 and a second switch 47. The switches 46, 47 serve as preselector switches for the temperature to which the heating pad 2, 30 and/or the heating pad segments 33 to 36 are to be heated up. The switch areas of the switches 46, 47 may be subdivided for optical indication of the patient's lying position (for example lateral position). This means that when one of the switches 46, 47 is depressed, an optical signal will appear in part of its actuating area, indicating whether the heating pad 2 is heated in such a way that it emits sufficient heat for a patient resting on the heating pad 2 either in lateral position or on his back.

The heating system for operating tables illustrated in FIG. 1 operates as follows.

For putting the heating system 1 into operation, one first connects the heating pad 2 to the regulating and control unit 3, using the cable 10. Thereafter, the master switch is actuated to switch on the regulating and control unit 3 which can be operated selectively with a.c./d.c. current of between 12 Volts and 240 Volts. By depressing the first switch 46 or the second switch 47 selectively, one then preselects the temperature to which the heating pad 2 is to be heated up. The temperatures assigned to the switches are, for example, 34° C. for the first switch 46 and 38° C. for the second switch 47. If the first switch 46 is depressed, for example, luminous diodes 48 will light up in the luminous fields 40, 41, 42, 43 indicating that the heating segments 12a, 12b, 12c, 12d are heated up and are operating free from trouble. Once the desired temperature of T=34° C. has been reached, luminous diodes 49 light up in the luminous fields 40, 41, 42, 43 indicating that the predetermined heating temperature has been reached in the individual heating segments 12a, 12b, 12c, 12d, and the heating system is switched off automatically. As soon as the temperature drops below the desired value of T=34° C., the heating system is switched on again so that the desired temperature is constantly maintained in the heating segments.

The temperature prevailing in the individual heating segments 12a, 12b, 12c, 12d is monitored by the temperature sensors 19 installed in the heating pad 2. The temperature is measured in each heating segment at two points of the heating pad 2, 30, and the values so measured are continuously supplied as actual values to the control and regulating unit 3. Based on the higher temperature value measured in the heating segment, the regulating and control unit 3 then adjusts the heating power of the heating pad 2, 30.

The electric circuitry of the regulating and control unit 3 corresponds to that described by DE-PS 34 34 772. The disclosure content of that publication is incorporated herein as being essential to the present invention, but is extended insofar as means are provided for comparing the actual temperature values of the different heating segments 12a, 12b, 12c, 12d measured at a given time before any regulation of a heating segment 12a, 12b, 12c, 12d is effected. The system then always makes use of the higher of two temperature values for regulating purposes.

If, alternatively, the second switch 47 is depressed, which may be assigned a temperature of T=38° C., for example, then the heating pad 2 is heated up until the temperature measured by the temperature sensors 19 in the heating pad 2 is equal to T=38° C. As soon as the temperature sensors 19 transmit to the regulating and control unit 3 a temperature value of 38° C., the heating of the heating pad 2 switched off automatically by the regulating and control unit 3, and luminous diodes 50 light up in the luminous fields 40, 41, 42, 43. The regulating and control unit 3 monitors the temperature in the heating fields and keeps the temperature constant, i.e. the heating is switched on and off automatically, as required. In the event the temperature of T=38° C. should be exceeded in any of the heating segments 12a, 12b, 12c, 12d and the temperature should rise above a threshold value of, for example, T=41° C., a luminous diode 41, to which a permanent acoustic signal is coupled, will light up in the respective luminous field 40 to 43. In the event the temperature threshold value of T=41° C. should be further exceeded in any of the heating segments 12a, 12b, 12c, 12d, and the temperature measured should reach a value of T=45° C., for example, an additional luminous diode 52 will light up which indicates by a flashing signal, combined with an intermittent acoustic signal, that the admissible heating temperature in the heating pad 2 has been exceeded in an inadmissible manner.

An additional safety feature becomes operative when a total heating period of, say, 15 min. has been exceeded. The monitoring and control unit 3 will then automatically switch off the heating of the heating pad 2.

The regulating and control unit 3 is further suited for detecting resistance differences in the different heating segments 12a, 12b, 12c, 12d and for switching off either individual heating segments 12a, 12b, 12c, 12d or the whole heating system when any of the electric conductors 18 are defective or interrupted or if unwanted bridging should occur between the electric conductors 18.

The heating capacity for a heating segment amounts, for example, to 30 Watt, at a voltage of U=24 Volts.

The heating pad 2, 3, is manufactured in different sizes for use on standard operating table tops and on operating tables for children. In addition, the heating pad 2, 30 may be used as heating pad for any other hospital application.

We claim:

1. A heating system for an operating table comprising a multi-layer heating pad (2) comprising at least one heating segment (12a, 12b, 12c, 12d), each segment being adapted for being electrically heated, said heating pad being pervious to X-rays and having means for connection to control and regulating unit means (3) for controlling and/or regulating electrical heating current necessary for achieving an adjustable temperature, said heating pad (2) having a heating conductor (16) comprising a resistor (18) having a specific electrical resistance and means defining a helical pattern of winding of the resistor about a carrier (17) made from an electrically non-conductive material, for enabling said heating conductor to stretch in an axial direction, said non-conductive material having rubber-elastic mechanical properties in the temperature range of between 10° celsius and 200° celsius, said heating pad (2) being formed from different layers, each layer intimately bonded to form a composite material, said heating conductor (16) being embedded in a first layer (13) and having a thickness not more than 10% to 20% greater than an outer diameter of the heating conductor (16), said first (13) layer being surrounded by a second layer (14) of silicone rubber, said first and second layers (13, 14) having largely identical material properties, and fabric layer means (15) disposed between the first and second layers (13, 14) and forming a composite structure with the first and second layers, for limiting elastic expansion of the first and second layers, the total thickness of the said heating pad (2) being about 5 mm in the area of the heating segments and about 8 mm in a marginal area.

2. A heating system for an operating table comprising a multi-layer heating pad (2) comprising at least one heating segment (12a, 12b, 12c, 12d) each segment being adapted for being electrically heated, said heating pad being pervious to X-rays and having means for connection to control and regulating unit means (3) for controlling and/or regulating electrical heating current necessary for achieving an adjustable temperature, said heating pad (2) having a heating conductor (16), disposed along a neutral center plane of the heating pad, comprising an aluminum wire of circular cross-section having a specific electrical resistance and means defining a helical pattern of winding of the aluminum wire about a carrier (17) for enabling said heating conductor to stretch in an axial direction, said carrier being made from an electrically non-conductive silicone rubber material, said non-conductive silicone rubber material having rubber-elastic mechanical properties in the temperature range of between 10° celsius and 200°, celsius said heating pad (2) being formed from different layers, each layer intimately bonded to form a composite material, said heating conductor (16) being embedded in a first layer (13) and having a thickness not more than 10% to 20% greater than an outer diameter of the heating conductor (16), said first (13) layer being surrounded by a second layer (14) of silicone rubber, said first and second layers (13, 14) having largely identical material properties, and fabric layer means (15) disposed between the first and second layers (13, 14) and forming a composite structure with the first and second layers, for limiting expansion of the first and second layers, the total thickness of the said heating pad (2) being approx. 5 mm in the area of the heating segments and approx. 8 mm in a marginal area.

3. A heating system for an operating table comprising a multi-layer heating pad (2) comprising at least one heating segment (12a, 12b, 12c, 12d), each segment being adapted for being electrically heated, said heating pad being previous to X-rays and having means for connection to control and regulating unit means (3) for controlling and/or regulating electrical heating current necessary for achieving an adjustable temperature, said heating pad (2) having a heating conductor (16) disposed in a meander-like line pattern along a neutral center plane of the heating pad, comprising an aluminum wire of circular cross-section having a specific electrical resistance and means defining a helical pattern of winding of the aluminum wire about a carrier (17) for enabling said heating conductor to stretch in an axial direction, said carrier being made from an electrically non-conductive silicone rubber material, said non-conductive silicone rubber material having rubber elastic mechanical properties in the temperature range of between 10° celsius and 200° celsius, each layer intimately bonded to form a composite material, said heating conductor (16) being embedded in a first layer (13) and having a thickness not more than 10% to 20% greater than an outer diameter of the heating conductor (16), said first (13) layer being surrounded by a second layer (14) of silicone rubber, said first and second layers (13, 14) having largely identical material properties, and fabric layer means (15) disposed between the said first and second layers (13, 14) and forming a composite structure with the adjacent layers, for limiting elastic expansion of the first and second layers, the total thickness of the said heating pad (2) being about 5 mm in the area of the heating segments and about 8 mm in a marginal area, said first layer (13) being an electrically non-conductive silicone rubber layer having good thermal conductivity and having a rubber-elastic behavior similar to that of the carrier (17), said second layer being an electrically non-conductive silicone rubber layer reinforced in marginal areas and having a surface forming a composite structure with a third layer (25), said third layer including material means for eliminating electric charges, said heating system further comprising temperature sensors (19) including two semiconductor resistors with high negative temperature coefficients per heating segment (12a, 12b, 12c, 12d), arranged in the heating pad (2) between the meander-like lines of the heating conductor (16).

4. A heating system according to claim 3 wherein said temperature sensors (19) include connection wires previous to X-rays.

5. A heating system according to claim 3 wherein the aluminum wires of the heating conductors (16) of the heating segments (12a, 12b, 12c, 12d) are connected in parallel, the connection wires of the temperature sensors (19) are united in pairs, and the heating system further comprises electric conductor means connected to the third layer (25), for eliminating electrostatic charges.

6. A heating system according to claim 3 wherein the wires of the heating conductors are bunched and said heating system further comprises means, disposed at point of exit of the bunched wires from the said first layer (13), for preventing kinking of the bunched wires.

7. A heating system according to claim 6 wherein the bunched wires are surrounded outside the said first layer (13) by a flexible sheathing, temperature-resistant in the temperature range of 10° celsius to 200° celsius, and the bunched wires terminate in a plug (21) adapted for sealing by a cap (22).

8. A heating system according to claim 3 wherein marginal areas of a lower surface of the heating pad include closure tape means (32) for attaching heating segments thereto.

9. A heating system according to claim 8 wherein the control and/or regulating unit (3) means comprises a plurality of inputs for lines from the heating pad (2; 30) and segments (33 to 36).

10. A heating system according to claim 3 wherein said heating pad includes means, defining a slot therein and extending from a narrow side of the heating pad, for enabling the attachment of diverse additional segments.

11. A heating system according to claim 3 further comprising insulating mat means (4) for covering the heating pad (2; 30) and/or the segments (33 to 36).

12. A heating system according to claim 3 wherein the regulating and/or control unit means (3) includes a display (8) comprising first and second pre-selector switch means (46, 47) for controlling the temperature of the said heating pad (2; 30) and the segments (33 to 36), and luminous field means (40 to 45) for indicating the operative state, the operating condition and any faulty condition of the individual segments (12a, 12b, 12c, 12d).

13. A heating system for an operating table comprising a multi-layer heating pad comprising at least one heating segment having a heating conductor therein comprising a resistor wound on a non-conductive carrier and means, defining a helical path of winding of said resistor about said carrier, for enabling said heating conductor to stretch in an axial direction, said carrier being formed from a material having rubber-elastic mechanical properties for enabling, in combination with the helical wound resistor, the heating conductor to stretch in the axial direction, each heating segment comprising different layers, with each layer intimately bonded to form a composite material, said heating conductor being embedded in a first layer, said first layer being surrounded by a second layer of silicone rubber, said first and second layers having generally identical material properties and fabric layer means disposed between the first and second layers, for limiting elastic expansion of the first and second layers.

14. A heating system according to claim 13 wherein each heating segment comprises means, defining parallel placement of a plurality of conductors, for enabling the heating pad to be tightly rolled without damage to the plurality of conductors.

* * * * *

UNITED STATES PATENT AND TRADEMARK OFFICE
CERTIFICATE OF CORRECTION

PATENT NO. : 5,138,138
DATED : August 11, 1992
INVENTOR(S) : Wolfgang Theilacker; Hans-Peter Stihler; Axel Stihler and Josef Burkert It is certified that error appears in the above-identified patent and that said Letters Patent is hereby corrected as shown below:

On the title page at [73] the Assignee should be identified as:

Stihler Electronic Medizintechnische Gerate Produktions und Vertriebs GmbH, Fed. Rep. of Germany and
HORN GmbH & Co. KG, Fabrik fur Metall-Silicon-und Teflonverarbeitung, Fed. Rep. of Germany.

Signed and Sealed this

First Day of March, 1994

*Attest:*

BRUCE LEHMAN

*Attesting Officer*  *Commissioner of Patents and Trademarks*